United States Patent [19]
Church et al.

[11] Patent Number: 5,277,197
[45] Date of Patent: Jan. 11, 1994

[54] MICROPROCESSOR CONTROLLED SYSTEM FOR UNSUPERVISED EMG FEEDBACK AND EXERCISE TRAINING

[75] Inventors: John Church, Ft. Lauderdale; William Hassel, Davie, both of Fla.

[73] Assignee: Physical Health Device, Inc., Pompano Beach, Fla.

[21] Appl. No.: 917,683

[22] Filed: Jul. 22, 1992

Related U.S. Application Data

[63] Continuation of Ser. No. 333,269, Apr. 5, 1989, abandoned, which is a continuation-in-part of Ser. No. 938,830, Dec. 8, 1986, abandoned.

[51] Int. Cl.$^5$ ............................................. A61B 5/04
[52] U.S. Cl. ................................................... 128/733
[58] Field of Search ............... 128/733, 736, 774, 775, 128/781, 782, 776, 777, 778, 780; 340/573; 33/571, 512; 73/865.1, 379; 272/129; 364/413.02, 413.27, 551.01

[56] References Cited

U.S. PATENT DOCUMENTS 4,367,752 1/1983 Jimenez et al. ................. 128/782
4,396,019 8/1983 Perry, Jr. .......................... 128/778
4,665,928 5/1987 Linial et al. ...................... 128/782
4,667,513 5/1987 Konno ............................. 128/774

Primary Examiner—Kyle L. Howell
Assistant Examiner—J. P. Lacyk
Attorney, Agent, or Firm—Eric P. Schellin

[57] ABSTRACT

An exercise training system for prompting a user for stereo typed exercise and recording the intensity of the exercise, the training system consisting of an electromyographic sensor member which produces a rectified and time averaged signal forming a muscle force signal, the sensor member being provided with at least one electrode that is positioned adjacent to the user's muscle group for indicating muscle force of that muscle group, and a control member having a clock for measuring time intervals, and an alerting member for alerting the user that an exercise period has started as determined by the clock for a predetermined time interval loaded into the control means, whereby the user in response to the alerting member contracts and relaxes a predetermined muscle group and the muscle force used in the exercise is sensed by the electromyographic sensor.

15 Claims, 8 Drawing Sheets

Fig. 1
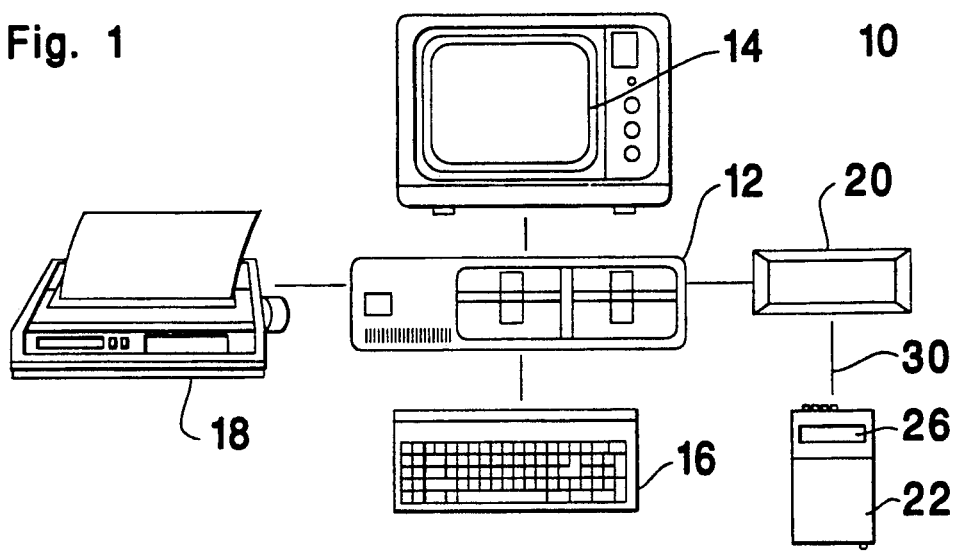
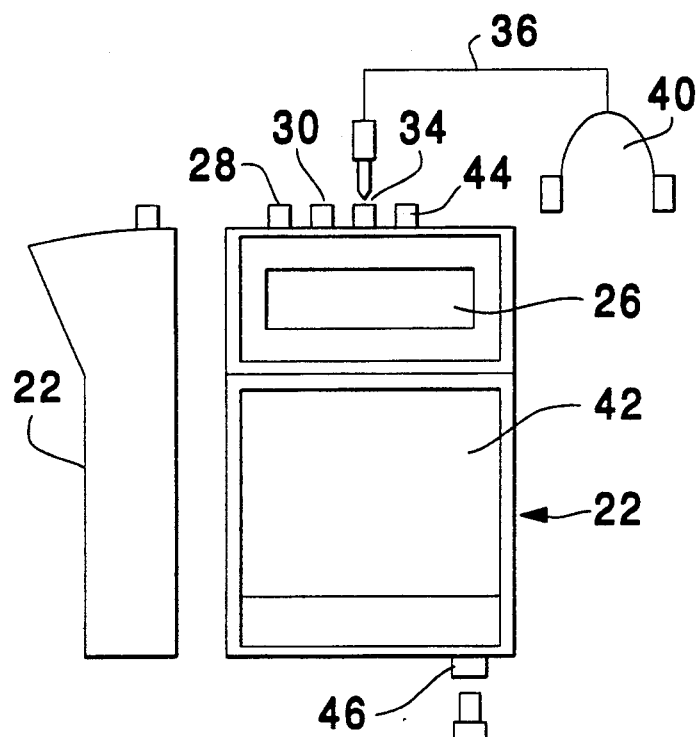
Fig. 2B
Fig. 2A
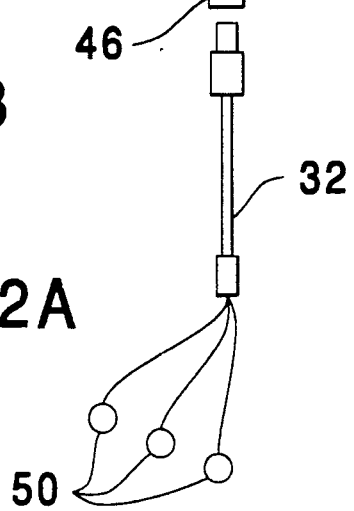

Strip Chart Mode

Bar Graph Mode

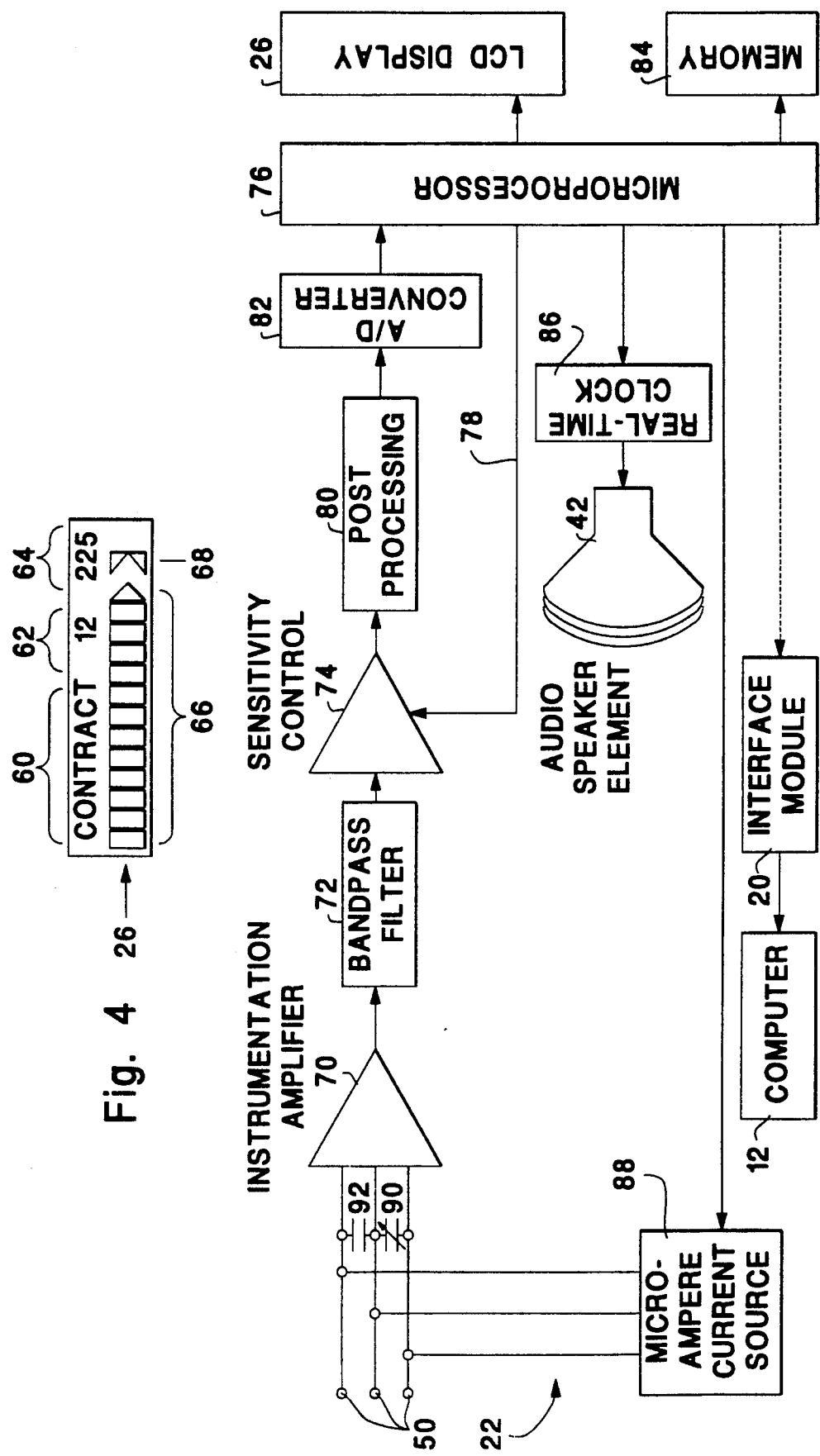

-Legend- $N_I$ IS INTEGRATION INTERVAL, FOR THE PRESENT INVENTION=0.1 SECOND.

$X_H$ IS % OF CURRENT FULL SCALE RANGE CRITERION FOR DECREASING SENSITIVITY, FOR PRESENT INVENTION=85%

$X_L$ IS % OF CURRENT FULL SCALE RANGE CRITERION FOR INCREASING SENSITIVITY, FOR PRESENT INVENTION=15%

$A_S$ IS SENSITIVITY CHANGE INCREMENT, FOR THE PRESENT INVENTION = 2.0

```
07:39:30 PM            XYZ CLINIC              Tue Jan 5, 1988
Version 3.1        [1] Open Patient File Menu  Patient: BILL
```

[1] [E]dit Bio-Feedback Parameters
[2] [S]tart Clinical Session

[3] [R]eview Most Recent Session
[4] Review / Print Session [H]istory

[5] Edit Patient [I]nformation
[6] [C]hange Patient File

Enter selection...

Physical Helth Devices, Inc., Miami, Florida

MAIN MENU

[1.1] Edit Bio-Feedback Parameters

```
Patient File.. BILL              Created on. 12/19/87
Patient Name.. JOHN DOE          Last used... 1/ 5/88
Muscle........ FOREARM FLEXOR    Session #... 9
```

Bio-Feedback Parameters

```
Mode (F/I).......Facilitory   Prompting (C/P)........ Prompted
Goal (F/A/N).....Fixed        Contract time (secs)... 10
Goal Value uV*RMS  0.5        Relax time (secs)...... 10
Auto-Range mode..Auto-range   Number of repititions.. 20

Audio Feedback... Tone        Time Constant (secs)... 0.25
Visual Feedback.. Vert-Bar
Damping Factor... 9
```

Muscle or comment

EDIT FEEDBACK PARAMETERS

Fig. 9

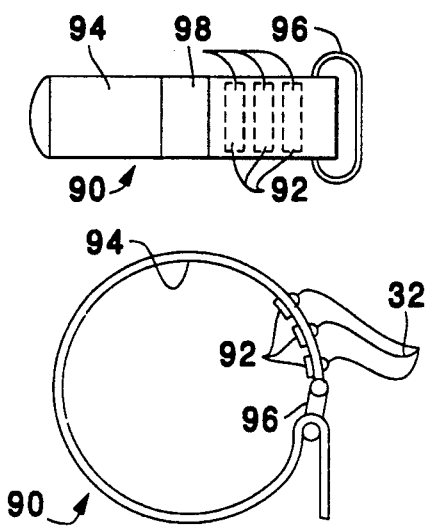
Fig. 10A
Fig. 10B
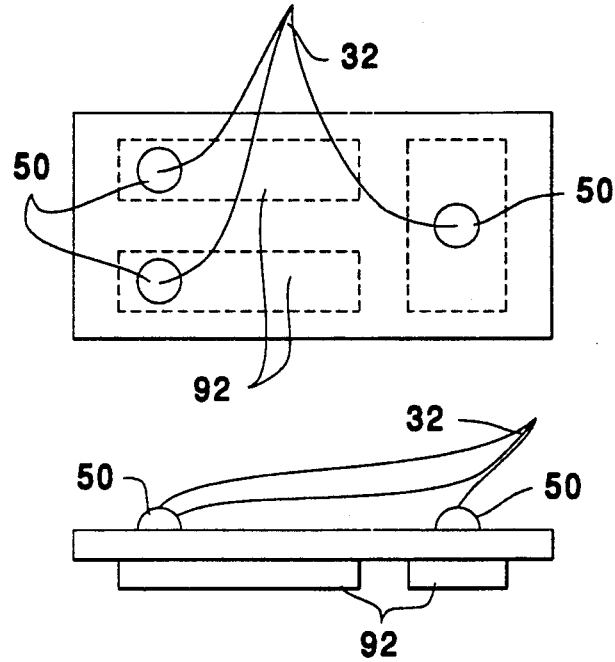
Fig. 11A
Fig. 11B
Fig. 12A
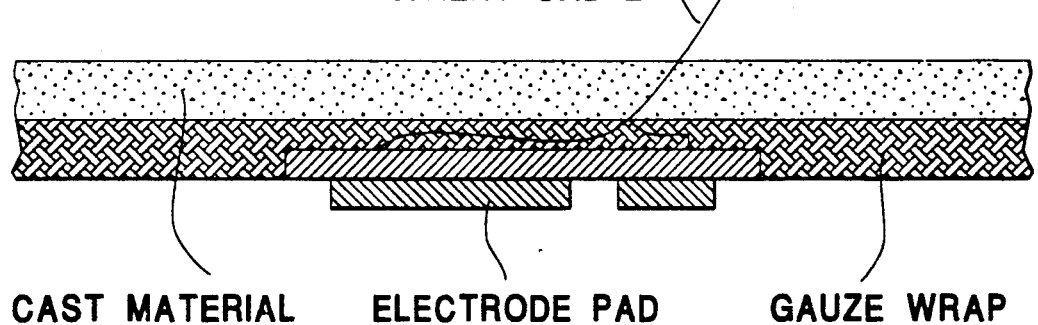
CAST MATERIAL    ELECTRODE PAD    GAUZE WRAP
Fig. 12B
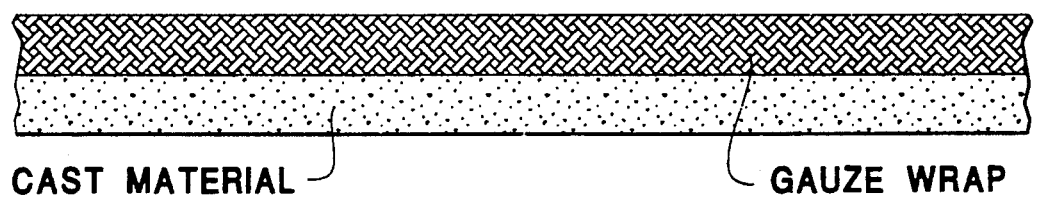
CAST MATERIAL    GAUZE WRAP Fig. 13
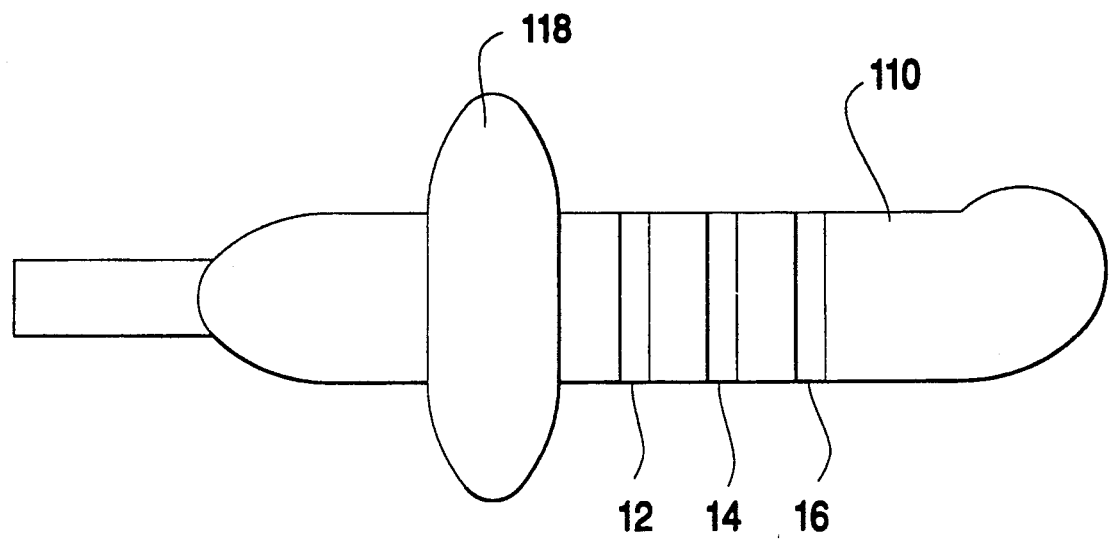
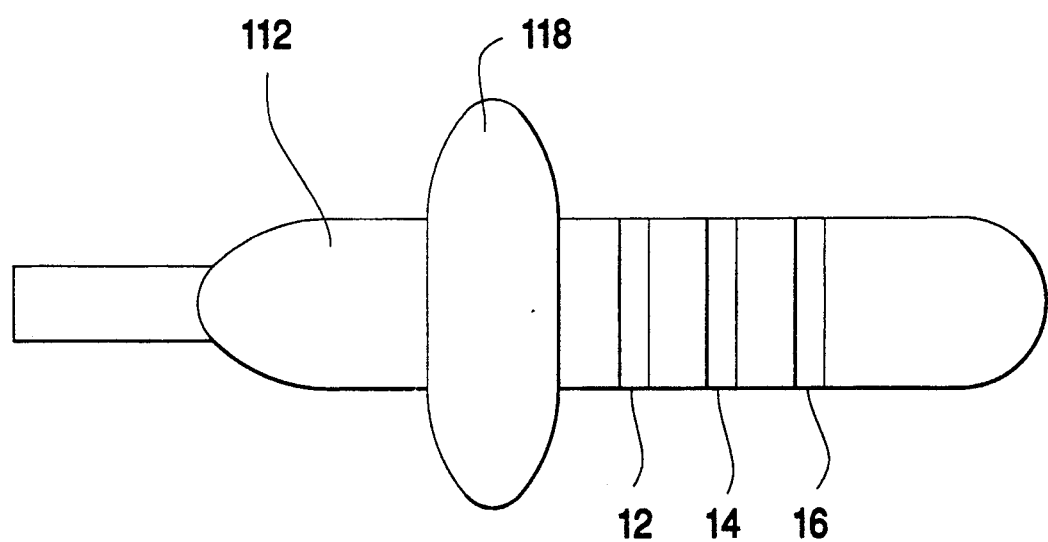
Fig. 14

MICROPROCESSOR CONTROLLED SYSTEM FOR UNSUPERVISED EMG FEEDBACK AND EXERCISE TRAINING

This application is a continuation of application Ser. No. 07/333,269, filed Apr. 5, 1989, now abandoned, which is a continuation-in-part application of my co-pending patent application Ser. No. 06/938,830 filed Dec. 08, 1986 now abandoned, claiming benefit under 35 U.S.C. §121, and entitled A Lifting Monitoring And Exercise Training System; the entire disclosure of the application is incorporated herein by reference.

BACKGROUND OF THE INVENTION

1. Field of the Invention

The invention relates to an improved neuromusclar training system for prompting stereotyped muscular control on the part of a user and quantitatively recording the user's performance and method for prompting stereotyped muscular control on the part of a user and quantitatively recording the user's performance, and more particularly, the invention is directed to electromyography (EMG) in the use of instrumentation for the visual and auditory cues to the user as to the degree of muscular control, as a function of the magnitude of myoelectric signals associated with the contraction and relaxation of skeletal muscles that is used in the diagnosis and treatment of a variety of medical conditions.

The invention relates further to a system for applying EMG biofeedback and/or exercise training of an individual in an unsupervised environment in which the individual's muscular performance and compliance to the prescribed biofeedback and exercise program may be monitored by a medical or therapist authority, and the method of constructing the system thereof as more particularly described herein.

2. Description of the Prior Art

Electromyographic (EMG) activities and measurements are those developed or derived by transcutaneous measurements taken across the skin, i.e., on or upon the surface of the skin, by use of electrodes connected in an electronics circuit or system and fed back to the patient or subject in the form of visual and/or auditory exteroceptive signals; transcutaneous electromyographic neouromuscular feedback has proven to be an important and often indispensable tool in the acquisition and retraining of volitional control of muscular action and coordination in many areas of medicine and related therapy. EMG feedback is also found to serve as an adjunctive quantitative evaluation of the effectiveness of therapeutic treatment of specific muscles or of muscle groups in terms of rate and degree of therapeutic progress.

Also, recent research indicates that EMG feedback exerts a positive influence on directed exercise in terms of increased muscle mass of the exercised portion of the body, and EMG feedback coupled with exercise produces significant gains in muscle mass beyond exercise alone. Patients with immobilized fractures of body extremities, as one example, are found to suffer decreased blood flow and muscle mass in a confined limb, and which often requires lengthy and sometimes painful rehabilitation following removal of a cast or brace. Such patients are candidates for EMG feedback-assisted isometric exercise training with the EMG electrode means embedded in the cast or brace and positioned superficially over the muscle or muscles being trained.

Medical literature references are known that indicate patients being candidates for kinds of prescribed and extensive EMG feedback and exercise programs are patients having these kinds of conditions: cerebral vascular accident or and head trauma; spinal cord injuries; peripheral nerve damage; industrial accidents undergoing work-hardening for lower back or other muscles; orthopaedic and physical therapy programs involving rehabilitation; urinary and fecal incontinence; athletics and sports related injuries; and requirements for relaxation training for headache, chronic pain, psychotherapeutic relaxation, and muscle hypertension and spasm.

Various prior art EMG biofeedback systems and the like, as well as apparatus and method of their construction in general, are found to be known and exemplary of the U.S. prior art are the following:

U.S. Pat. No. 3,641,993 Gaarder
U.S. Pat. No. 3,905,355 Brudney.

Brudney discloses equipment for processing detected EMG activity such that it may be provided to a subject in a psychophysiologically meaningful manner for the treatment of disorders of voluntary movement. Gaarder discloses a more generalized scheme for exteroceptive feedback of EMG activity by converting the magnitude of the processed signal to a logarithmic form to obviate the need for constant readjustment of various gain settings potentially disruptive to the therapeutic process and confusing to the clinician who may have only a hazy concept of the meaning of various gain adjustments (Gaarder, column 1, lines 20-25, and 40-45).

These patents or known prior uses teach and disclose various types of exercise training systems and devices of sorts and of various manufactures and the like as well as methods of their construction, but none of them whether taken singly or in combination disclose the specific details of the combination of the invention in such a way as to bear upon the claims of the present invention.

SUMMARY OF THE INVENTION

Clinical EMG devices and systems for visual and auditory feedback are most often large, complex devices and systems designed for in-clinic use; EMG feedback training on a patient therefore requires skilled supervision. This type of system limits the total amount of feedback training for a patient as it predicates training on only a periodic basis and is ill-suited for home use. The problem here is further compounded for severely motor-impaired individuals as clinical visits may be very inconvenient and feedback training in the home by a qualified therapist is found to be quite expensive. It should be noted here that 'device' and 'system' will generally be used interchangeably throughout this specification.

Complexity of such systems is due in part because transcutaneously measured human EMG widely varies in electrical potential from several microvolts to several thousand microvolts depending on the muscle being examined, the muscle's enervation, the specific medical condition, and other parameters relating to the patient. This wide variability has thereof has necessitated adjustment for different sensitivity ranges of the EMG measurements.

It is found that portable EMG devices designed for unsupervised home-use by a patient are purely passive devices that must be adjusted at the clinic for sensitivity and "zeroing" of the background or baseline signals for the specific muscle and medical condition, and therefore do not accomodate evolving changes in the patient's motor function which may cause the device to be "out of range." Some (e.g., Gaarder) of them address this issue by providing visual feedback signals which are a logarithmic function of detected EMG.

Use of a logarithmic scale is not a wholly acceptable solution as it produces nonlinear sensitivity (i.e., less sensitive to changes in EMG at higher levels of EMG). Optimally, the visual feedback signal should be directed proportional to the magnitude or energy of the detected EMG signal.

Such devices intended for home-use often comprise a "goal" which may be manually set at the clinic to provide a target level of performance which the patient attempts to achieve, either by facilitation or inhibition of volitional EMG. This goal is usually displayed on the visual device member, and if audio feedback is also used, may produce changes in audio feedback once the goal is achieved. In these devices there is no provision for automatic adjustment of the goal to meet the patients evolving capabilities and requirements.

Portable devices do not have separate operating modes to optimize applications for different types of training, e.g., facilitory vs. inhibitory training. Beyond instructions provided at the clinic, the patient receives no prompting of when to begin or end a prescribed or stereotyped volitional motor action. These devices have no means by which the patient's compliance to prescribed training programs may be monitored or any means of providing a record of the patient's home-use training performance to the therapist.

Transcutaneous EMG feedback devices nesessitate the use surface recording electrodes which invariably require preparation of the skin (shaving, cleaning with alcohol) and, often, application of electrode gel prior to electrode placement. For home-use, achievement of stereotyped electrode placement (very critical to meaningful feedback training) requires detailed instruction for the therapist and is difficult for motor-impaired individuals. Also, these "traditional" types of electrodes are either disposable (producing additional cost to the patient) or reusable (which require cleaning after each use) further complicating the practical realization of unsupervised EMG feedback training.

Useful EMG feedback measurement depends on the integrity of any cabling system which commutates the feedback device to the electrodes as well as sufficient electrode contact to the skin. Home-use EMG feedback devices in current use have no facility for testing electrode contact or electrical integrity to automatically alert the patient to problems when they occur.

An object, advantage and feature of the invention is to provide a novel EMG device which provides a practical, compact, battery-operated, portable electronic, microprocessor controlled "patient module" for unsupervised EMG visual and auditory feedback training and compliance monitoring outside the clinical environment.

Another object of the invention is directed further to an EMG device that essentially has no control beyond a START/STOP buttom to initiate and terminate home-use sessions.

Also an object of the invention is to provide a simple and direct EMG device that is programmable (via desktop mini-computer) by the clinical authority for a variety of different operating modes, therefore able to be custom programmed for the patient's specific requirements.

Another object of the invention is to provide a novel and improved EMG device that automatically adjusts EMG sensitivity to the patient's current and evolving motor levels without sacrifice of linearity or resolution.

Another object of the invention is directed further to an EMG device that can be programmed to automatically prompt the patient to perform stereotyped, volitional motor actions.

A further object of the invention is directed to an EMG device that incorporates a liquid crystal display (LCD) for linear visual feedback of the EMG levels as well as prompting for stereotyped volitional action.

Another object of the invention is to provide an EMG device that incorporates a speaker element which emits an audio signal whose frequency varies monotonically with the EMG level to produce audio feedback.

Another object of the invention seeks to provide an EMG device that logs the time and days of patient use as an index of compliance to the prescribed feedback training program for periodic review by the clinician, therapist or medical authority.

Another object of the invention provides an EMG device that logs descriptive statistical parameters of each home-use session, as an index of training performance/progress for periodic review by the clinician, therapist or medical authority.

An additional object of the invention provides an EMG device that alerts the patient to problems in electrical integrity and/or electrode contact so that corrective measures may be taken.

Another object of the invention contemplates an EMG device that can be programmed for individualized use and periodically interrogated by the use of a computer in the clinic. The data "uploaded" to the computer during module interrogation includes the compliance and statistical training history and may be reviewed by the clinician on the computer monitor, printed on a line printer for hard-copy and/or stored on magnetic media (computer disc or tape) for archival of the patient's permanent data file.

Another object of the invention is directed further to an EMG device that, in clinical use, acts as a "front end" EMG data acquisition means so that visual feedback of high resolution on the computer monitor may be utilized for in-clinical evaluation, assessment, and feedback training.

While the present invention seeks to accomodate "traditional" varieties of surface-recording electrodes, the electrode system of the invention comprises conductive fabric electrodes which aid greatly in stereotyped electrode placement, do not require application of conductive electrode gel and which in most cases requires no skin preparation. These are applied with great ease and require only simple laundering in prolonged use In typical use, once the therapist has determined that the EMG feedback training is indicated, the patient will receive the EMG evaluation in the clinic. Here the patient module is connected to electrodes on the patient and is also connected to a computer via an interface module which provides electrical isolation of the patient. The patient's EMG is displayed visually on the computer monitor in one of several possible visual feedback modes. The therapist adjusts (via computer) the module's various operating parameters as well as the placement of the electrodes on the patient so that the displayed the EMG signal is optimized with respect to training requirements. This procedure is often iterative and may take an entire clinical session to achieve optimal configuration. At this point the therapist will make a series of the EMG measurements utilizing the patient module and computer, for evaluation purposes, and usually in the absence of any visual or auditory feedback provided to the patient. In most cases these clinical operating parameters are the same as those programmed into the module for home-use training. The therapist programs the module for home-use and so instructs the patient in the use of the module, eloctrode placement, replacement of batteries, and like maintenance details for the system.

After the patient has performed home-use training with the module, the patient will return to the clinic for periodic visits. In these visits the therapist will interrogate the module for compliance and performance history, and will perform further in-clinic evaluation of the evoked EMG levels. The therapist will review module data for anomalies in compliance and performance and will compare the current, non-feedback evaluation to earlier evaluations. In this way the therapist may review trends in compliance, performance and degree of motor learning and/or muscle strengthening generalized to the non-feedback environment. The therapist may elect to adjust operational parameters and/or electrode placement in response to evolving therapeutic requirements. Cycles of clinical evaluation and home-use training are repeated until the therapist feels that no further gains are to be expected from continued training.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWINGS

FIG. 1 is a schematic arrangement of a microprocessor controlled system providing for unsupervised EMG feedback useful in exercise training and illustrating a typical installation of the system according to a preferred embodiment and best mode of the present invention.

FIG. 2A is a schematic illustration showing a plan view of the patient module of FIG. 1 and embodying the concepts of the invention.

FIG. 2B is a side view of the patient module.

FIG. 4 shows an LCD display during a prompted contract/relax session on the patient module.

FIG. 5 is an electronics circuit block diagram of the microprocessor controlled patient module providing for unsupervised EMG feedback useful in exercise training according to the invention.

FIGS. 8 and 9 show illustrations of menu screens on the computer monitor for a main menu and for editing feedback parameters, respectively.

FIGS. 10A and 10B show respective plan and elevation views of a fabric electrode belt which may be used with the patient module of the invention.

FIGS. 11A and 11B show respective plan and elevation views of fabric electrode pad which may be applied to the skin with material such as tape on a bandage.

FIGS. 12A and 12B show respective plan and elevation views of a patient cable, leads and electrode pad fabricated directly into a cast with one end free for connection to the patient module.

FIG. 13 is a side view of a cylindrical mounting assembly for the sensing electrode that is adapted to be inserted into a female's vagina.

FIG. 14 is a side view of cylindrical mounting assembly for the sensing electrode that is adapted to be inserted into a user's anus.

DESCRIPTION OF A PREFERRED EMBODIMENT OF THE INVENTION

Figure 3A:
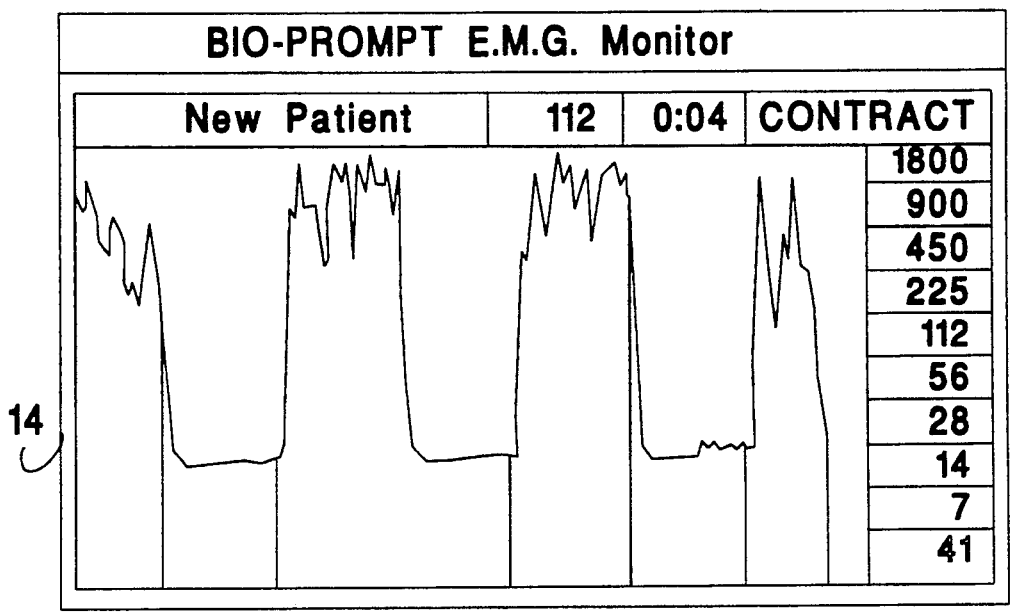
FIGS. 3A and 3B show displays of various visual feedback modes for in-clinic use of the patient module in conjunction with the computer and monitor for high resolution visual feedback thereof.

Referring now to the drawings there is shown in FIG. 1 a computer system or microprocessor controlled system 10 for unsupervised EMG feedback and exercise training for clinical use, and including a computer 12, a computer video monitor 14, a keyboard 16, and a printer 18 which may be an IBM-based or IBM clone system; an interface module 20 provides communications between the patient module 22 and the microprocessor system 10, the interface module 20 also providing electrical isolation of the patient module 22 for minimizing possible electrical hazards when the computer system 10 is used in clinical mode where the patient module 22 is connected to both the patient (not shown) and the computer 12 that comprise the computer system 10.

With the computer system 10, the interface module 20 and the patient module 22 so connected, a program loaded into the computer 12 is used to program and/or interrogate or read data in the patient module 22.

FIG. 2A illustrates certain details and connections of the patient module 22 and in which are shown an liquid crystal display (LCD) 26; a START/STOP push button 28 which the patient presses to initiate and terminate home-use sessions; a communications jack 30 which accepts a cable 32 from the interface module 20 to perform communications between the computer system 10 and the patient module 22; an audio out jack 34 which may accept a connector 36 from optionally connected audio headphones 40, and if headphones 40 are not used, the audio feedback signal is emitted from a speaker element 42 internal to the module 22; a "stim trigger" 44 may be programmed to actuate an auxiliary functional electrical stimulation (FES) device when a preprogrammed EMG threshold is exceeded; a patient cable jack 46 communicates the patient cable 32 to the patient module 22, the patient cable 32 connecting to a variety of different electrode types via snap connectors 50.

If, in addition, the patient module 22 is connected to the patient via cable 32 and electrodes or connectors 50, a computer program can cause the patient module 22 to perform or act as the sole source of visual and auditory feedback.

Figure 3B:
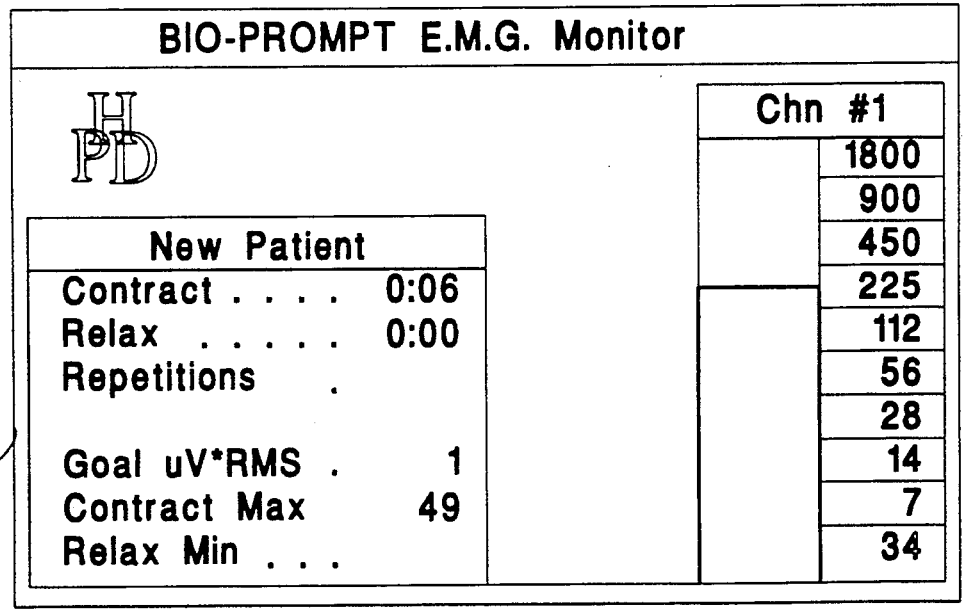

FIGS. 3A and 3B show the various visual feedback modes as displayed on the computer video monitor 14. In FIG. 3A a strip chart mode represents an "oscilloscope-type" graph where the EMG level is displayed as a function of time. FIG. 3B shows visual display of a bar graph whose magnitude corresponds to real-time EMG levels.

In both the clinical and the home-use applications, there are a variety of programmable operating modes and parameters which influence the character of feedback provided to the patient. These are feedback modes comprising a facilitory mode or an inhibitory mode; a prompting mode comprising a contract/relax mode or a continuous mode; a therapeutic goal parameter comprising a fixed goal mode or an auto-goal mode or a no goal mode; an audio feedback parameter comprising a silent mode or a tone mode; and a damping factor parameter.

The facilitory mode is used in cases where the aim of therapy is motor facilitation, i.e., in learning to vocationally evoke higher levels of EMG in muscular contraction.

The inhibitory mode is used in cases where the aim of therapy is motor inhibition, i.e., in learning to volitionally reduce the EMG levels in muscular relaxation.

The choice of feedback mode influences automatic ranging of sensitivity, automatic goal establishment and audio feedback. These are described later and below.

In the contract/relax mode operation, the patient is alternately prompted to contract and relax the muscle(s) being trained by visual display of the words "contract" and "relax". The duration of half-cycles of the contract and relax modes are programmable as is the total number of contract/relax cycles which comprise the total duration of the session.

In the continuous mode the subject receives or generally needs no prompting.

The therapeutic goal parameter comprises display of a "target" level which the patient attempts to achieve by virtue of either muscle contraction or relaxation. With the fixed goal option the therapist programs a specific goal level in microvolt units. This goal is displayed on the visual feedback means (LCD) as shown in FIG. 4 at the programmed level according to the current full scale sensitivity range.

In the auto-goal mode of operation, the position of the goal within the visual full scale range is automatically adjusted to new levels as the subject becomes more successively capable of achieving it. The method by which this is realized is discussed later below.

In the no-goal mode the operation of feedback proceeds without the use of any goal.

In the silent mode the auditory feedback is disabled.

In the tone mode an audio feedback tone is emitted from the computer system 10, the patient module 20 or the optional audio headphones 40. The audio feedback signal is a constant tone modulated by a variable duty cycle carrier whose frequency is monotonically related to the EMG level, i.e., higher EMG = higher frequency; lower EMG = lower frequency. Additional audio affect is also linked to the therapeutic goal and feedback mode as follows:

In facilitory mode the tone becomes constant (100% carrier duty cycle) as long as the EMG level is above the current goal level.

In inhibitory mode the tone is switched off, producing silence, as long as the EMG level remains below the current goal level.

The damping factor mode, for the present invention, is analogous to the technical or scientific term "time constant" or "RC constant" and refers to the amount of time for the feedback signal to respond to changes in the actual EMG level. Damping is thus achieved by application of a moving average, uniformly weighted, "box car" digital low pass filter to the digitized EMG signal. The filter widths from 0.1 second to 3.0 seconds are programmable.

Any combination of the above parameters and modes as described in detail above may be used, though not all combinations may lend themselves to practical uses.

FIG. 4 illustrates an example of the display 26 during a prompted contract/relax session. Prompt 60 is the visual means to "cue" the patient to alternately contract and relax the muscle being trained. In the prompted mode the display timer 62 displays the remaining time interval available of the contract or relax half-cycle. In the continuous mode the timer counts down the remaining minutes and seconds of the session. The displayed level 64 is the current EMG reading in microvolts-rms.

The bar graph 66 is the visual feedback of the EMG levels. An "expansion" of the bar to the right produces by higher EMG levels with increased muscle tension while "contraction" of the bar to the left occurs during lower EMG levels associated with muscle relaxation. Movement of the bar on the LCD display 26 is equivalent to bar graph responses and deflection of the strip chart display on the computer monitor 14 in clinical mode operation.

The goal 68 is the displayed therapeutic goal which the patient attempts to achieve. In the facilitory mode, the goal, unless currently surpassed by movement of the bar to the right with muscular contraction, will usually be to the right of the "tip" of the bar as shown. In the inhibitory mode the goal will ordinarily be displayed to the left of the tip of the bar unless the bar has "shrunk" sufficiently to the left with muscle relaxation.

During both home-use and clinical sessions, the patient module 22 is used to test for electrical integrity and electrode connection or continuity and then displays a "CHECK ELECTRODES" indicia or message should problems be detected.

FIG. 5 is an electrical block diagram of the electronics in the patient module 22. Instumentation amplifier 70 receives signals from electrode connectors 50 and amplifies the EMG signal from the electrodes and provides high input impedance and high common mode rejection ratio (CMRR), and the filter 72 filters the signal to sensitivity control 74 which allows control of the signal gain by the automatic ranging scheme realized in the program running the microprocessor 76. While sensitivity control 74 can be realized in a variety of ways, the present invention uses a control member comprising an amplification network providing nine discrete ranges of sensitivity; full scale ranges of visual feedback correspond to the EMG levels of 7, 14, 28, 56, 112, 225, 450, 900, and 1800 microvolts-rms (root-mean-square) detected at the electrodes of connectors 50. The important issue here is the control over line 78 of sensitivity control 74 by the microprocessor 76 to provide appropriate automatic ranging of the EMG levels in the context of practical facilitory mode and the inhibitory mode of the EMG feedback.

Post processing network 80 provides additional signal conditioning by comprising additional amplification, additional bandpass filtration and AC to true RMS conversion. Analog to digital converter 82 converts the amplified analog EMG signal output of the post processing network 80 to digital values read by the microprocessor 76. In the present invention the analog to digital converter 82 is intergrated into the microprocessor 76 of the patient module 22. An alternative scheme within the scope of the invention includes a voltage-to-frequency converter coupled to a timer circuit read by the microprocessor 76. The source of visual feedback is seen in the LCD display 26.

Memory 84 stores the microprocessor program in the patient module 22 and includes a "work area" for calculations and stores compliance and EMG data descriptive of the user's performance. The real-time clock 86 "wakes up" the microprocessor 76 at programmed times to alert the patient when it is times to commence scheduled, home-use sessions. The clock also generates the tone, modulated by the microprocessor 76 for audio feedback. The audio feedback signal is emitted by speaker 42.

A microampere current source 88 is periodically activated by the microprocessor 76 to produce a sinusoidal voltage across the electrodes connected to the patient. The voltage produced is related to the electrical impedance between the electrodes, is processed by members 72, 74, 80, 82, 76 converted and read by the microprocessor 76 to measure interelectrode impedance as a test of electrical cabling integrity and electrode contact-to the patient.

Trim capacitor 90 is factory adjusted to balance load capacitance 92 with parisitic capacitance within the patient cable commutated via the patient jack 46 to amplifier input connectors 50 to minimize pickup pf common mode interference and thus reduce the likelihood of saturation of the instrumentation amplifier.

Figure 6:
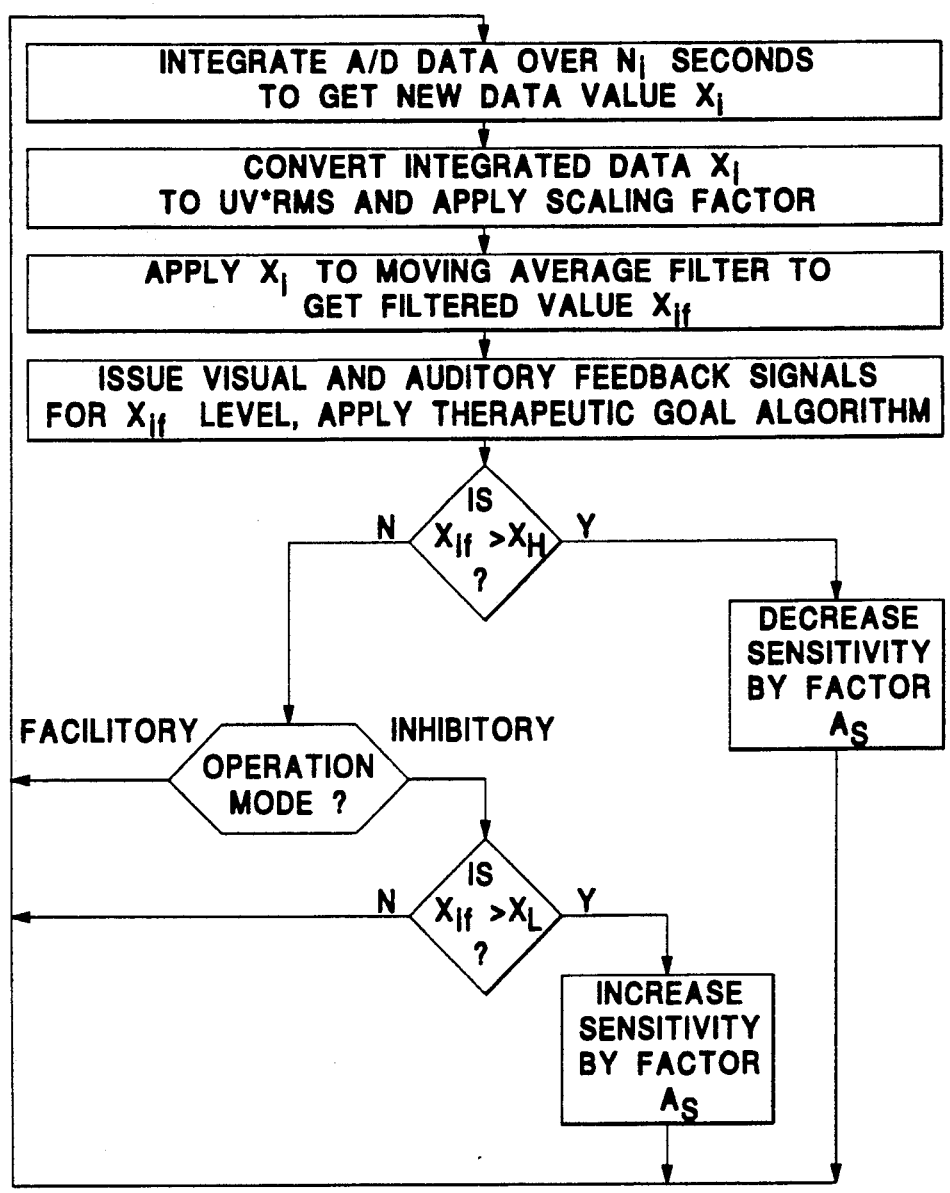
FIG. 6 is a flow chart of the microprocessor program of the patient module providing for unsupervised EMG feedback useful in exercise training and automatic ranging of the EMG signal.

FIG. 6 illustrates the generalized flow chart of the program of the microprocessor 76 for automatic ranging of the EMG signal.

In the present arrangement increase of sensitivity represents a doubling of gain of the analog signal at the sensitivity control 74 and decreasing sensitivity represents a halving of gain. In another realization sensitivity control comprises more incremental changes in sensitivity, i.e., sensitivity increment is much less than 2, e.g., 1/256. It should be noted here that consideration of integrated values $X_i$ or $X_{ij}$ as candidates for descriptive statistics, timing for display of prompts, interelectrode impedance calculations, and the like, or any other sundry routines for memory access, communications, and so on, are obvious issues to one skilled in the communications art.

Figure 7:
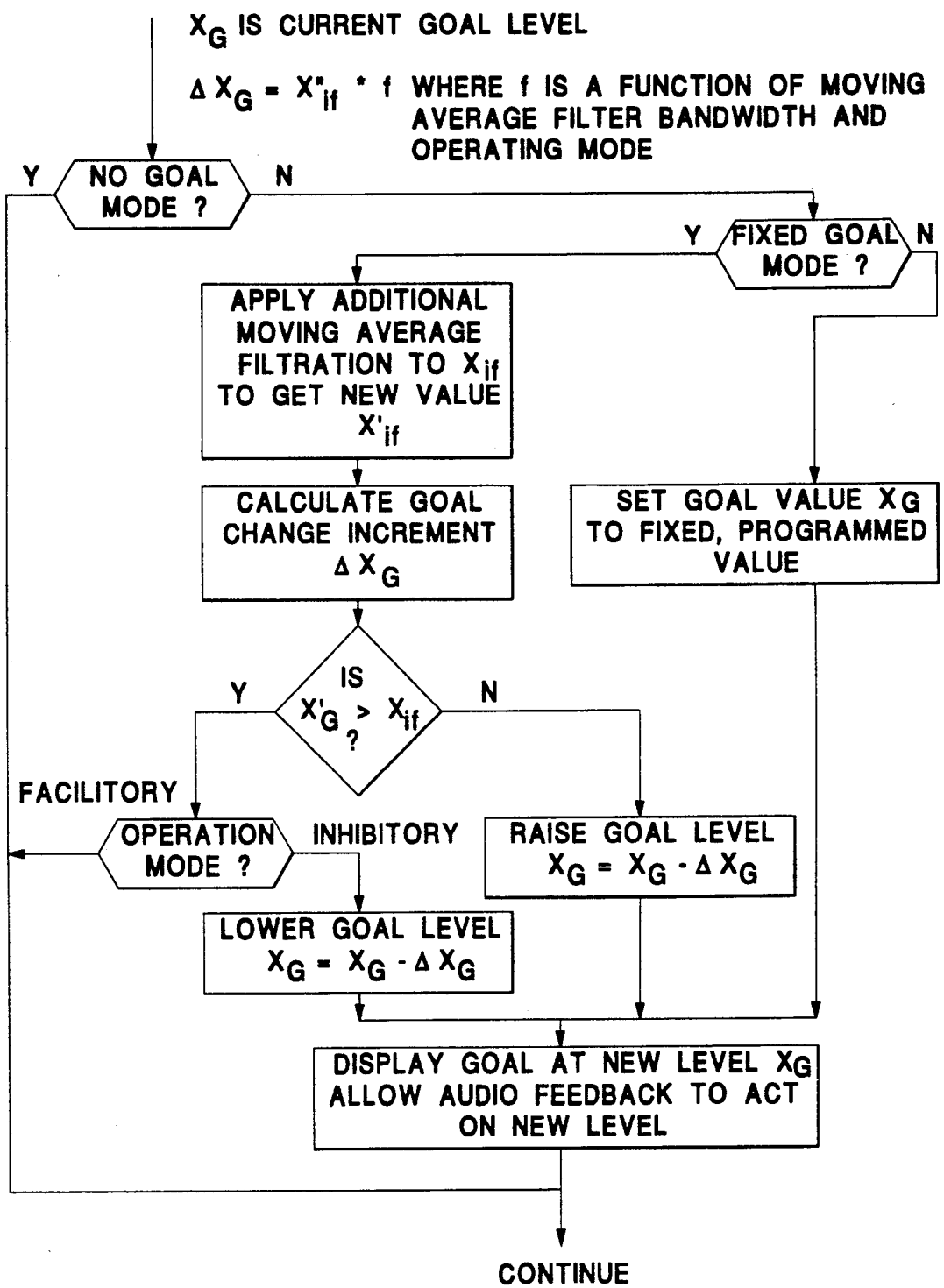
FIG. 7 is a generalized flow chart of the microprocessor program of the patient module for automatic goal establishment according to the invention.

FIG. 7 illustrates the generalized flow chart of the program of the microprocessor 76 for automatic goal establishment.

Use of the computer system 10 to read or program the patient module 22, perform clinical sessions and/or review, print or archive clinical or home-use data is accomplished via an interactive program loaded in the computer. There are an infinite number of ways in which such a program may or can be written. FIGS. 8 and 9 reflect, respectively, a Main Menu of the program and the Editing of Feedback Parameters for the present invention and are presented here for purposes of demonstrating and illustrating the scope of the invention.

FIGS. 10A and 10B illustrate the configuration of a webbing material or fabric belt 90 for supporting electrode(s) which may be used with the patient module 22. Conductive silver contact pads 92 of the connectors 50 are attached to self-gripping material 94, such as VELCRO ®, a well-known hook and loop gripping or coupling material, which forms the belt 90. The belt 90 is fabricated in several lengths and widths to accomodate EMG detection on the arms, legs, lumbar, torso, and head over the entire range of anthropomorphic dimensions. To fasten the belt 90, the end of the belt 90 is passed through ring clasp 96, pulled tight and fastened to the body of the belt 90. Patient cable leads 32 are commutated to the conductive pads via snap connectors 50. Elastic material 98 helps facilitate uniform and pad contact where, as in most cases, the region of the body where the belt 90 is to be secured is not uniformly cylindrical.

FIGS. 11A and 11B illustrate a fabric electrode pad which may be applied with adhesive material such as tape, to external areas of the body such as the top of the shoulders, which do not lend themselves to the use of the belt 90. The fabric electrode pad also may be applied in a cast as illustrated in FIGS. 12A and 12B with the patient cable and leads fabricated directly into the cast with one end free for connection to the patient module.

FIGS. 13 and 14 illustrate probes for sensing EMG feedback of vaginal and rectal muscle groups and directed to electrode mounting assemblies that were designed to be inserted into naturally occuring body orifices. These assemblies are generally cylindrical and have three stainless steel electrode bands located about their circumferences. The embodiment illustrated in FIG. 13 comprises a cylindrical member 110 which is inserted into a female vagina so that the female patient can monitor the exercise of associated vaginal muscles. The embodiment illustrated in FIG. 14 comprises cylindrical member 112 and is inserted into a patient's anus for monitoring a patient's exercise of the anal sphincter muscles. Both units are made from injected molded plastic, and are provided with depth gauges 118 which can be adjustably positioned and fixed on the cylindrical members by a therapist.

The apparatus of the microprocessor controlled system 10 of the invention may be so constructed and arranged in its various component parts that it may be assembled as a kit or in kit form.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters patent is:

1. A neuromuscular training system for alerting a user when a training session is to begin and recording the performance of the session, the training system comprising an electromyographic sensor which produces an electrical signal representative of EMG activity,
the sensor being provided with at least one electrode that is positioned adjacent to a muscle group of the user for indicating muscle force of that muscle group and wherein the at least one electrode is secured about a member which is adapted and constructed to be inserted into a natural orifice of the user for measuring the muscle force,
an amplifier connected to the sensor for receiving the electrical signal representative of EMG activity and amplifies the electrical signal to provide an amplified output,
a filter that receives the amplified output of the amplifier and provides a filtered output, a sensitivity control that receives the filtered output and provides a sensitivity controlled output.

a processing network that receives the sensitivity controlled output and provides a signal conditioned output, an analog-to-digital converter that receives the signal conditioned output and converts the signal conditioned output to a digital output, a microprocessor that receives the digital output and provides a processed output, a control means having a clock for measuring time intervals and that receives the processed output for alerting the user that an exercise period has started as determined by the clock for a predetermined time interval loaded into the control means and an alerting means for generating a tone, as modulated by the microprocessor, that provides an audio feedback signal, and a display means that receives the processed output for displaying the level of muscle ennervation exerted by the user and generated in the exercise period when contracting a muscle group adjacent to the electrode of the electromyographic sensor, the display means and the alerting means being also provided with a speaker for communicating the audio feedback signal to the user, whereby the user in response to the alerting means contracts and relaxes the muscle group and the level of muscle ennervation is sensed by the electromyographic sensor.

2. The neuromuscular training system of claim 1 further comprising a recording means that receives the processor output for recording the EMG signals indicating muscle ennervation from the electromyographic sensor and time of the muscle force signals.

3. The neuromuscular training system of claim 1 wherein the display means that receives the processor output and comprises a means including a visible bar graph or liquid crystal display.

4. The neuromuscular training system of claim 1 wherein the control means that receives the processor output and includes means for providing data for recording on a permanent data medium.

5. The neuromuscular training system of claim 2 wherein the recording means that receives the processor output and comprises an electronic memory means.

6. The neuromuscular training system of claim 5 wherein the microprocessor is provided with an interface which can be coupled to a means for programming exercise parameters into the electronic memory means and for tabulating a history or pattern of the user's performance by interrogating the electronic memory means.

7. The neuromuscular training system of claim 6 wherein the muscle force signal of the electromyographic sensor is an analog signal representative of total myoelectric energy that is converted to a digital signal by an analog to digital converter before being directed to the microprocessor.

8. The neuromuscular training system of claim 1 wherein the electromyographic sensor is provided with two or more electrodes.

9. The neuromuscular training system of claim 1 wherein the the member is a cylindrical member.

10. A neuromuscular training system for alerting a user when a training session is to begin and recording the performance of the session, the training system comprising an electromyographic sensor which produces an electrical signal representative of EMG activity, the sensor being provided with at least one electrode that is positioned adjacent to a muscle group of the user for indicating muscle force of that muscle group and wherein the at least one electrode of the electromyographic sensor is secured to a webbing or fabric means which can be applied to the user so that the electrodes are located adjacent to a muscle group, an amplifier connected to the sensor for receiving the electrical signal representative of EMG activity and amplifies the electrical signal to provide an amplified output, a filter that receives the amplified output of the amplifier and provides a filtered output, a sensitivity control that receives the filtered output and provides a sensitivity controlled output, a processing network that receives the sensitivity controlled output and provides a signal conditioned output, an analog-to-digital converter that receives the signal conditioned output and converts the signal conditioned output to a digital output, a microprocessor that receives the digital output and provides a processed output, a control means having a clock for measuring time intervals and that receives the processed output for alerting the user than an exercise period has started as determined by the clock for a predetermined time interval loaded into the control means and an alerting means for generating a tone, as modulated by the microprocessor, that provides an audio feedback signal, and a display means and recording means of the performance of the session, for displaying the level of muscle ennervation exerted by the user and generated in the exercise period when contracting a muscle group adjacent to the electrode of the electromyographic sensor, the display means and the alerting means being also provided with a speaker for communicating the audio feedback signal to the user, whereby the user in response to the alerting means contracts and relaxes the muscle group and the level of muscle ennervation is sensed by the electromyographic sensor.

11. The neuromuscular training system of claim 10 wherein the fabric means is gauze.

12. The neuromuscular training system of claim 11 wherein the control means, the recording means and the display means are located in a housing.

13. The neuromuscular training system of claim 10 wherein the electromyographic sensor means is mounted within a patient module supported by a fabric belt means.

14. The neuromuscular training system of claim 13 wherein the electrodes are conductive electrode silver contact pad means and are attached to self-gripping material such as a hook and loop coupling or self-gripping material and forms part of the belt means.

15. The neuromuscular training system of claim 13 wherein the belt means is fabricated in any of various lengths and widths to accomodate EMG detection of the arms, legs, lumbar, torso, and head over the entire range of anthropomorphic dimensions.

* * * * *